(12) United States Patent
Chien (10) Patent No.: US 11,663,927 B2
(45) Date of Patent: May 30, 2023

(54) FOOD QUANTUM TRACKING TOOLS AND METHODS RELATED THERETO

(71) Applicant: Tso-Cheng Chien, S. Hamilton, MA (US)

(72) Inventor: Tso-Cheng Chien, S. Hamilton, MA (US)

(*) Notice: Subject to any disclaimer, the term of this patent is extended or adjusted under 35 U.S.C. 154(b) by 415 days.

(21) Appl. No.: 16/872,257

(22) Filed: May 11, 2020

(65) Prior Publication Data

US 2020/0372826 A1     Nov. 26, 2020

Related U.S. Application Data

(60) Provisional application No. 62/846,564, filed on May 10, 2019.

(51) Int. Cl.
| | |
|---|---|
| *G09B 19/00* | (2006.01) |
| *H04N 5/92* | (2006.01) |
| *G06T 11/00* | (2006.01) |
| *G06F 16/51* | (2019.01) |
| *G16H 20/60* | (2018.01) |

(52) U.S. Cl.
CPC ......... *G09B 19/0092* (2013.01); *G06F 16/51* (2019.01); *G06T 11/00* (2013.01); *G16H 20/60* (2018.01); *H04N 5/9201* (2013.01)

(58) Field of Classification Search
None
See application file for complete search history.

(56) References Cited

U.S. PATENT DOCUMENTS

| | | | |
|---|---|---|---|
| 11,138,901 B1* | 10/2021 | Angel | G01G 19/4146 |
| 2014/0072672 A1* | 3/2014 | Nisbet | A23L 19/09 |
| | | | 426/112 |
| 2016/0071423 A1* | 3/2016 | Sales | G06K 9/6201 |
| | | | 434/127 |
| 2020/0090248 A1* | 3/2020 | Zeng | G06Q 50/12 |
| 2022/0409139 A1* | 12/2022 | Ben-Tsur | A61B 5/073 |

\* cited by examiner

*Primary Examiner* — Phirin Sam
(74) *Attorney, Agent, or Firm* — JWIP & Patent Services, LLC; Jacob G. Weintraub, Esq.

(57) ABSTRACT

The present invention relates to novel methods, tools and systems that provide an individual with the ability to define a personalized portion and evaluate food in real-world situations to offer guidance to the individual on the amount of the food the individual should eat as part of a controlled and consistent diet based on food volume. In particular, the methods, tools and systems of the present invention define food quanta personalized to the user, and further utilizes augmented reality to overlay a selected food quantum on real-world food in order to guide the user to select a definable food quantum, e.g., to achieve a dietary goal.

27 Claims, 5 Drawing Sheets

FOOD QUANTUM TRACKING TOOLS AND METHODS RELATED THERETO

RELATED APPLICATIONS

This application claims priority to U.S. Provisional Patent Application No. 62/846,564, filed on May 10, 2019; the entirety of which is incorporated herein by reference.

BACKGROUND OF THE INVENTION

Monitoring one's own health, particularly using mobile devices, has become ubiquitous in today's society. From step counting to heartrate monitoring to food tracking, numerous tools have been developed for an individual to monitor their daily activity using applications developed to be used in a self-guided manner. Many of these tools or applications provide simple data for the user to understand such as count tallies, while certain applications offer analytics of this data based on trends identified in the data.

Step and heartrate may be straight forwardly counted and measured against a desired and trackable step count or heartrate goal; as these are based on number-to-number comparative analysis. However, portion control is not so simply tabulated, given that calculation of a meal through tabulation of calorie information for identified food items is not necessarily useful unless the individual eats the entire meal. However, a significant portion of people do not eat their entire meal, and consequently such method would inaccurately reflect their caloric intake. Moreover, this calculation of caloric intake would provide little guidance on what portion of a meal an individual should eat to reflect a specific desire to eat within consistent defined restrictions, particularly as compared with other meals.

In this respect, while food items in general may be quantified by calorie count, it is far more difficult to capture and personally regulate an individual's personal portion control with consistency. Known food journal applications offer a user the ability to pictorially capture food items in a log, but caloric calculations are based on the food present, rather than the specific portion consumed (or to be consumed). Further, even volume estimation by the user of the food captured in a pictorial log is not capable of consistent comparison given that the variability of the capture window of the image and the angle of each of the pictures would obscure relative comparison.

Putative portion monitoring and control tools and systems have evolved over the last decade from food trackers to food identifiers using artificial intelligence in conjunction with database records to identify a specific food item from images. Some of these tools even offer guidance as to the health of the identified food item. Further, more complex systems have been used to calculate the volume of food items in limited and regulated circumstances using either complicated image capture systems under defined environmental conditions or adding reference markers for calibration and identification of single volume units; neither of which are suitable for real world day-to-day activities.

In fact, there are no tools that offer individuals the ability to define a personalized portion and evaluate food in real-world situations to offer guidance to the individual on the amount of the food the individual should eat as part of a controlled and consistent diet based on food volume. As such, there remains significant need for food tracking tools that provide such guidance for daily portion control in real world scenarios, for example, to achieve a dietary goal.

SUMMARY OF THE INVENTION

Accordingly, the present invention is directed to novel methods, tools and systems that provide an individual with the ability to define a personalized portion and evaluate food in real-world situations to offer guidance to the individual on the amount of the food the individual should eat as part of a controlled and consistent diet based on food volume. In particular, the methods, tools and systems of the present invention define food quanta personalized to the user, and further utilize augmented reality to overlay a selected food quantum on real-world food in order to guide the user to select a definable food quantum, e.g., to achieve a dietary goal.

As such, one aspect of the present invention provides a food quantum tracking tool comprising a machine-readable medium having instructions stored thereon for execution by a processor to perform a method comprising the steps of: defining a food quanta series for a user; storing the defined food quanta on a second machine-readable medium; selecting a single food quantum from the stored food quanta series; and overlaying the selected food quantum on real-world food (RWF) using augmented reality without using a reference marker or reference-based imaging, such that the user is guided to select a definable food quantum, e.g., to achieve a dietary goal.

Another aspect of the present invention provides a method of food quantum tracking. The method comprises the steps of: defining a food quanta series for a user; storing the defined food quanta; selecting a single food quantum from the stored food quanta series; and overlaying the selected food quantum on real-world food (RWF) using augmented reality without using a reference marker or reference-based imaging, such that the user is guided to select a definable food quantum, e.g., to achieve a dietary goal.

BRIEF DESCRIPTION OF THE DRAWINGS

Advantages of the present apparatus will be apparent from the following detailed description, which description should be considered in combination with the accompanying drawings, which are not intended limit the scope of the invention in any way.

DETAILED DESCRIPTION OF THE INVENTION

Accurately tracking the amount of food an individual eats from a meal has proven very difficult in real-world environments. Moreover, the amount, or percentage, of that food eaten is not easily correlated on a meal to meal basis. Although food journaling has been the simplest approach to track the overall meal, it does not afford the user the ability to compare the consumed amount of one meal to a reference volume for consistency and dietary control. In this respect, the present invention is suitable for standardizing and personalizing a method of measuring the amount of food an individual consumes from a real-world meal by presenting and/or capturing a personalized portion, or food volume, using methods and tools that take advantage of augmented reality. The methods and tools presented herein are implemented regardless of an existing database of food and without using reference markers. Such tools and methods afford an individual access to customized information related to their well-being and diet, and the ability to use this information to make better decisions regarding their health. Furthermore, such tools are available for use on smart devices, such as smart phones, in real-world environments.

In this way, the present invention is directed to novel methods, tools and systems that provide an individual with the ability to define a personalized portion and evaluate food in real-world situations to offer guidance to the individual on the amount of the food the individual should eat as part of a controlled and consistent diet based on food volume. In particular, the methods, tools and systems of the present invention define food quanta personalized to the user, and further utilizes augmented reality to overlay a selected food quantum on real-world food in order to guide the user to select a definable food quantum, e.g., to achieve a dietary goal.

In specific embodiments described herein, anthropomorphic measurements may be captured for use in defining the food quanta, for example, the volume of a first of the user (e.g., calculated from the circumference of the fist), which studies have shown is equivalent to size of the stomach of the user. Moreover, beyond the ability to identify the volume of more than 2 fists, the present invention affords the ability to identify fractions of fists, which represent heretofore unattainable comparisons, especially in real-world situations.

The present invention, including systems, tools, and related methods will be described with reference to the following definitions that, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

The language "food quanta" is used herein to describe a series of food measurements defined as a multiple or fraction of an identified portion size based on a personalized volume defined for a user, e.g., a fist. It should be understood that the language "food quanta" is plural, while "food quantum" is singular, describing a single unit of an identified portion size based on a personalized volume defined for a user, e.g., a fist.

The term "interface" is art-recognized, and is used herein to describe a shared boundary across which two or more separate interfacing components are enabled to exchange information, which can be, for example, between: software components, computer hardware components, peripheral device components, humans, and combinations thereof. In specific embodiments, the term "interface" may be a user interface, e.g., a graphic user interface. Moreover, the operation of these separate components across the boundary, or vice versa, is referred to herein as "interfacing." In certain embodiments, the interfacing may be bi-directional. In other embodiments, the interfacing may be uni-directional.

The language "machine-readable medium" is art-recognized, and describes a medium capable of storing data in a format readable by a mechanical device (rather than by a human). Examples of machine-readable media include magnetic media such as magnetic disks, cards, tapes, and drums, punched cards and paper tapes, optical disks, barcodes, magnetic ink characters, and solid state devices such as flash-based, SSD, etc. Machine-readable medium of the present invention are non-transitory, and therefore do not include signals per se, i.e., are directed only to hardware storage medium. Common machine-readable technologies include magnetic recording, processing waveforms, and barcodes. In particular embodiments, the machine-readable device is a solid state device. Optical character recognition (OCR) can be used to enable machines to read information available to humans. Any information retrievable by any form of energy can be machine-readable. Moreover, any data stored on a machine-readable medium may be transferred by streaming over a network. In a particular embodiment, the machine-readable medium is a network server disk, e.g., an internet server disk, e.g., a disk array. In specific embodiments, the machine-readable medium is more than one network server disk.

The language "real-world" is used herein to describe an act or an item that exists in reality and is actually presented to an individual in course of every-day life, as opposed to being presented under controlled conditions with special requirements, being simulated or being theoretical. For example, "real-world food" is food that is presented to an individual physically during the course of every-day events, as opposed to under controlled or pre-defined conditions.

The language "reference-based imaging" is art-recognized, and is used herein to describe image comparison to an existing database, e.g., a stored food database.

The language "reference marker" is art-recognized, and is used herein to describe a separate reference point or standard item presented in (e.g., added to) the image itself, like a ruler or card, which is used to help guide the construction of a three-dimensional image of the real-world food.

The term "storing" is art-recognized, and is used herein to describe the act of saving data on a machine readable medium in a manner that such data is subsequently retrievable on that machine readable medium.

The language "sub-quanta" is used herein to describe a defined sub-quantity portion size within a quantum, for example, separated by the type of food group (e.g., protein, carbohydrate, dairy, fruit, vegetable, fat, and/or sugar).

The term "user" is used herein to describe any person that interfaces with the tools of the present invention described herein through electronic means, e.g., computer or mobile device. Such user may be credentialed or non-credentialed, and which may afford certain access rights in the interface based on such status.

II. Methods Of Food Quantum Tracking Of The Invention

One embodiment of the present invention, provides a method of food quantum tracking comprising the steps of:
- defining a food quanta series for a user;
- storing the defined food quanta;
- selecting a single food quantum from the stored food quanta series (e.g., user selection); and
- overlaying the selected food quantum on real-world food (RWF) using augmented reality without using a reference marker or reference-based imaging, such that the user is guided to select a definable food quantum, e.g., to achieve a dietary goal.

In certain embodiments of the methods of food quantum tracking of the present invention, the method further comprises the step of collecting additional information from the user. In particular embodiments, this collection further comprises requesting/receiving personal information. In specific embodiments, this personal information is selected from, for example, height, weight, gender, email address, and birthday.

In certain embodiments of the methods of food quantum tracking of the present invention, the method further comprises the step of capturing an image of the overlaid food quantum. In certain embodiments, the step of capturing the image utilizes a smart device camera capable of integrating augmented reality, e.g., an IPHONE® or android device. In particular embodiments, the method further comprises the step of storing said image to create a log, e.g., stored on a separate machine readable medium (e.g., selected from one or more solid state devices).

In certain embodiments of the methods of food quantum tracking of the present invention, the method further comprises the step of logging the food quantum selected (e.g., in conjunction with capturing an image of the overlaid food quantum). This logged food quantum may be tracked/monitored/stored along with additional information (e.g., weight, meal types, additional descriptive text) over a given time period (e.g., daily, weekly, monthly, yearly, etc.). Further, this information, in certain embodiments, may be analyzed for trends and predictive purposes to provide the user with analytics regarding their activities and their goals, for example in graphs and charts (e.g., bar charts and pie charts). For example, in a specific embodiment, weight prediction may be achieved by analyzing the correlation between collected data such as age, consumed quanta, and gender of a user; wherein the accuracy of the correlation may require certain amount of data collected by the user over time. In specific embodiments, correlation (trend) information from other users from the same gender and BMI may be used to make a reasonable prediction for a user.

A. Defining Food Quanta Series For User

In one step of the method, the step provides for defining a food quanta series for a user. The food quanta series may be personalized for each user. In particular, a food quantum, and the corresponding food quanta series may be defined by the user, or recommended for the user. In particular embodiments, the food quanta series is based on an anthropomorphic measurement of the user. In specific embodiments, the anthropomorphic measurement is the volume of a first of the user (e.g., calculated from the circumference of the fist).

In certain embodiments of the methods of food quantum tracking of the present invention, the step of defining a food quanta series for a user further comprises receiving input directly, providing a personalized defined volume. In certain embodiments, this receipt is based on a request for the information. In particular embodiments, this request may include, but is not limited to, scanning actual fist, utilizing a virtual ruler, or utilizing a physical ruler.

In certain embodiments of the methods of food quantum tracking of the present invention, the step of defining a food quanta series for a user further comprises receiving input to calculate a personalized defined volume. In certain embodiments, this receipt is based on a request for the information. In particular embodiments, the method further comprises the step of collecting shoe size information from the user, e.g., further comprising requesting/receiving personal information, including shoe size.

In certain embodiments of the methods of food quantum tracking of the present invention, the food quantum series may be selected from the food quanta 0.5×, 1×, 1.5×, 2.5×, or 3× of the first volume of the user.

In certain embodiments of the methods of food quantum tracking of the present invention, the method further comprises the step of identifying one or more sub-quanta within the food quantum. In certain embodiments, the method further comprises capturing and storing this sub-quanta, e.g., for data aggregation and/or analysis purposes. In particular embodiments, the sub-quanta are characterized based on type of food group (e.g., protein, carbohydrate, dairy, fruit, vegetable, fat, and/or sugar).

B. Storing Defined Food Quanta

In another step of the method, the step provides for storing the defined food quanta. Such storage is achieved using a machine-readable medium. This machine readable medium may be local on the user's device, cloud based, or both (e.g., mirroring information).

C. Selecting Single Food Quantum From Stored Food Quanta Series

In another step of the method, the step provides for selecting a single food quantum from the stored food quanta series. In this step, the user may select one food quantum of the food quanta series. Such selection may be a default selection (i.e., which may be changed by the user), or the user may have the opportunity to select each time without default.

In certain embodiments of the methods of food quantum tracking of the present invention, the method further comprises the step of selecting a second food quantum for comparison to the single food quantum; and overlaying the selected food quantum on real-world food using augmented reality without using a reference marker or reference-based imaging, to provide additional guidance to the user.

D. Overlaying Selected Food Quantum On Real-World Food (RWF) Using Augmented Reality In another step of the method, the step provides for overlaying the selected food quantum on real-world food (RWF) using augmented reality without using a reference marker or reference-based imaging. Augmented reality utilization provides a tool for the user to achieve an overlay image, spatially oriented over the real-world food independent of viewing angle or distance from the RWF, i.e., the overlay image does not require special distance or angle alignment given the augmented reality processing achieves this alignment by utilizing spatial imaging within a particular image.

In certain embodiments of the methods of food quantum tracking of the present invention, the selected food quantum overlay on the RWF is visualized using a digital display. In certain embodiments, the selected food quantum overlay is shown as a defined shape. This defined shape may be two dimensional (e.g., a 2D circle) or three dimensional (e.g., 3D sphere or anthropomorphic shape, such as a fist), in the visualization (e.g., with color notation based on the quantum size). In particular embodiments, the defined shape is three-dimensional for food that has significant depth, e.g., as in a bowl of food or a pile of food on a plate.

In certain embodiments of the methods of food quantum tracking of the present invention, the method further comprises overlaying the identified sub-quanta on real-world food (RWF) using augmented reality without using a reference marker or reference-based imaging, e.g., shown as a defined shape (e.g., 2D or 3D) and optionally with color notation. Such sub-quanta may be colored by distinct coloring with respect to the food quantum and/or each separate sub-quantum.

III. Food Quantum Tracking Tools Of The Invention

The methods of the present invention are useful as instructions stored on a machine-readable medium for execution by a processor to perform the method. In certain embodiments, the methods and tools of the present invention also make use and/or comprise a processor. Accordingly, any methods of the present invention, alone or in combination with other methods (such as those described herein or elsewhere) may be stored on a machine-readable medium for execution by a processor to perform the method. Such a composition comprises a food quantum tracking tool of the invention.

In this respect, the methods of food quantum tracking provide for guiding a user to select a definable food quantum. These methods comprise the steps of defining a food quanta series for a user; storing the defined food quanta; selecting a single food quantum from the stored food quanta series; and overlaying the selected food quantum on real-world food (RWF) using augmented reality without using a reference marker or reference-based imaging.

As such, one embodiment of the present invention provides a food quantum tracking tool comprising a machine-readable medium having instructions stored thereon for execution by a processor to perform a method comprising the steps of:

defining a food quanta series for a user;
storing the defined food quanta on a second machine-readable medium;
selecting a single food quantum from the stored food quanta series (e.g., user selection); and
overlaying the selected food quantum on real-world food (RWF) using augmented reality without using a reference marker or reference-based imaging, such that the user is guided to select a definable food quantum, e.g., to achieve a dietary goal.

In certain embodiments of the food quantum tracking tools of the present invention, the method further comprises the step of collecting additional information from the user. In particular embodiments, this collection further comprises requesting/receiving personal information. In specific embodiments, this personal information is selected from, for example, height, weight, gender, email address, and birthday.

In certain embodiments of the food quantum tracking tools of the present invention, the method further comprises the step of capturing an image of the overlaid food quantum. In certain embodiments, the step of capturing the image utilizes a smart device camera capable of integrating augmented reality, e.g., an IPHONE® or android device. In particular embodiments, the method further comprises the step of storing said image to create a log, e.g., stored on a third machine readable medium (e.g., selected from one or more solid state devices).

In certain embodiments of the food quantum tracking tools of the present invention, the method further comprises the step of logging the food quantum selected (e.g., in conjunction with capturing an image of the overlaid food quantum). This logged food quantum may be tracked/monitored/stored along with additional information (e.g., weight, meal types, additional descriptive text) over a given time period (e.g., daily, weekly, monthly, yearly, etc.). Further, this information, in certain embodiments, may be analyzed for trends and predictive purposes to provide the user with analytics regarding their activities and their goals, for example in graphs and charts (e.g., bar charts and pie charts). For example, in a specific embodiment, weight prediction may be achieved by analyzing the correlation between collected data such as age, consumed quanta, and gender of a user; wherein the accuracy of the correlation may require certain amount of data collected by the user over time. In specific embodiments, correlation (trend) information from other users from the same gender and BMI may be used to make a reasonable prediction for a user.

In certain embodiments of the food quantum tracking tools of the present invention, each of the machine-readable medium is selected from one or more solid state devices. In certain embodiments, each of the machine-readable medium is one or more network server disks.

Certain embodiments of the food quantum tracking tools of the present invention comprise a user interface. In particular embodiments, the user interface is a mobile application, e.g., available on smart devices (e.g., smartphones, or tablets). In particular embodiments, the user interface is a cloud based interface, e.g., based on iOS or Android platforms.

In certain embodiments of the food quantum tracking tools of the present invention, the first machine-readable medium, second machine-readable medium and the third machine-readable medium are the same machine-readable medium. In certain embodiments of the food quantum tracking tools of the present invention, the first machine-readable medium and the second machine-readable medium are the same machine-readable medium. In certain embodiments of the food quantum tracking tools of the present invention, the second machine-readable medium and the third machine-readable medium are the same machine-readable medium. In certain embodiments of the food quantum tracking tools of the present invention, the first machine-readable medium and the third machine-readable medium are the same machine-readable medium.

A. Defining Food Quanta Series For User

In one step of the method, the step provides for defining a food quanta series for a user. The food quanta series may be personalized for each user. In particular, a food quantum, and the corresponding food quanta series may be defined by the user or recommended for the user. In particular embodiments, the food quanta series is based on an anthropomorphic measurement of the user. In specific embodiments, the anthropomorphic measurement is the volume of a first of the user (e.g., calculated from the circumference of the fist).

In certain embodiments of the food quantum tracking tools of the present invention, the step of defining a food quanta series for a user further comprises receiving input directly, providing a personalized defined volume. In certain embodiments, this receipt is based on a request for the information. In particular embodiments, this request may include, but is not limited to, scanning actual fist, utilizing a virtual ruler, or utilizing a physical ruler.

In certain embodiments of the food quantum tracking tools of the present invention, the step of defining a food quanta series for a user further comprises receiving input to calculate a personalized defined volume. In certain embodiments, this receipt is based on a request for the information. In particular embodiments, the method further comprises the step of collecting shoe size information from the user, e.g., further comprising requesting/receiving personal information, including shoe size.

In certain embodiments of the food quantum tracking tools of the present invention, the food quantum series may be selected from the food quanta 0.5×, 1×, 1.5×, 2.5×, or 3× of the first volume of the user.

In certain embodiments of the food quantum tracking tools of the present invention, the method further comprises the step of identifying one or more sub-quanta within the food quantum. In certain embodiments, the method further comprises capturing and storing this sub-quanta, e.g., for data aggregation and/or analysis purposes. In particular embodiments, the sub-quanta are characterized based on type of food group (e.g., protein, carbohydrate, dairy, fruit, vegetable, fat, and/or sugar).

B. Storing Defined Food Quanta

In another step of the method, the step provides for storing the defined food quanta. Such storage is achieved using a machine-readable medium. This machine readable medium may be local on the user's device, cloud based, or both (e.g., mirroring information).

C. Selecting Single Food Quantum From Stored Food Quanta Series

In another step of the method, the step provides for selecting a single food quantum from the stored food quanta series. In this step, the user may select one food quantum of the food quanta series. Such selection may be a default selection (i.e., which may be changed by the user), or the user may have the opportunity to select each time without default.

In certain embodiments of the food quantum tracking tools of the present invention, the method further comprises the step of selecting a second food quantum for comparison to the single food quantum; and overlaying the selected food quantum on real-world food using augmented reality without using a reference marker or reference-based imaging, to provide additional guidance to the user.

D. Overlaying Selected Food Quantum On Real-World Food (RWF) Using Augmented Reality In another step of the method, the step provides for overlaying the selected food quantum on real-world food (RWF) using augmented reality without using a reference marker or reference-based imaging. Augmented reality utilization provides a tool for the user to achieve an overlay image, spatially oriented over the real-world food independent of viewing angle or distance from the RWF, i.e., the overlay image does not require special distance or angle alignment given the augmented reality processing achieves this alignment by utilizing spatial imaging within a particular image.

In certain embodiments of the of the food quantum tracking tools of the present invention, the selected food quantum overlay on the RWF is visualized using a digital display. In certain embodiments, the selected food quantum overlay is shown as a defined shape. This defined shape may be two dimensional (e.g., a 2D circle) or three dimensional (e.g., 3D sphere or anthropomorphic shape, such as a fist), in the visualization (e.g., with color notation based on the quantum size). In particular embodiments, the defined shape is three-dimensional for food that has significant depth, e.g., as in a bowl of food or a pile of food on a plate.

In certain embodiments of the of the food quantum tracking tools of the present invention, the method further comprises overlaying the identified sub-quanta on real-world food (RWF) using augmented reality without using a reference marker or reference-based imaging, e.g., shown as a defined shape (e.g., 2D or 3D) and optionally with color notation. Such sub-quanta may be colored by distinct coloring with respect to the food quantum and/or each separate sub-quantum.

IV. System Of The Invention

The food quantum tracking tools of the present invention, described herein, may be incorporated into systems, which may also comprise a smart device with a smart device camera capable of integrating augmented reality.

As such, another embodiment of the present invention provides a food quantum tracking system suitable for food quantum tracking comprising:
  a smart device with a smart device camera, e.g., an IPHONE® or android device; and
  a food quantum tracking tool of the present invention.

In certain embodiments, the smart device is a smartphone or a tablet.

V. Design Aspects of the Invention

Figure 1:
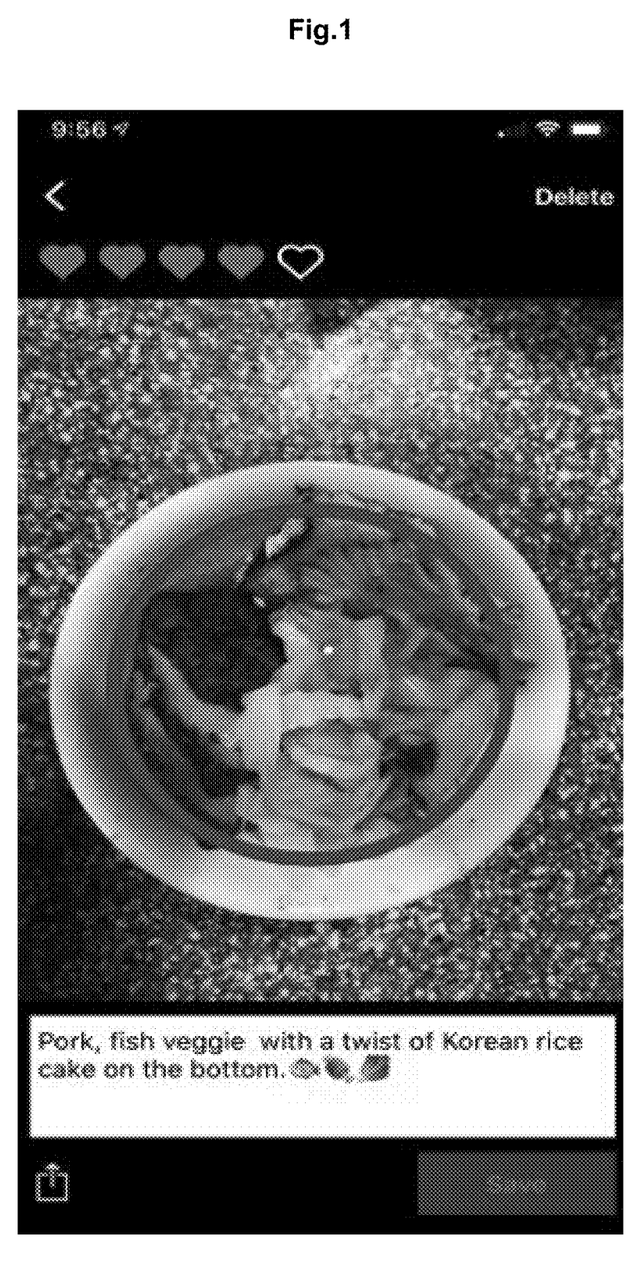
FIG. 1 is a depiction of the graphical user interface (GUI) of one particular embodiment of the tools of the present invention, depicting the visualized selected real-word food quantum overlay on a smart phone digital display as a defined 2-dimensional shape, i.e., a circle. In this particular embodiment, the GUI provides a text box to add description as well as a quality indication designated by the number of hearts filled in. The color of the circle corresponds to a specific of portion size, or quantum from the quanta series.
Figure 2:
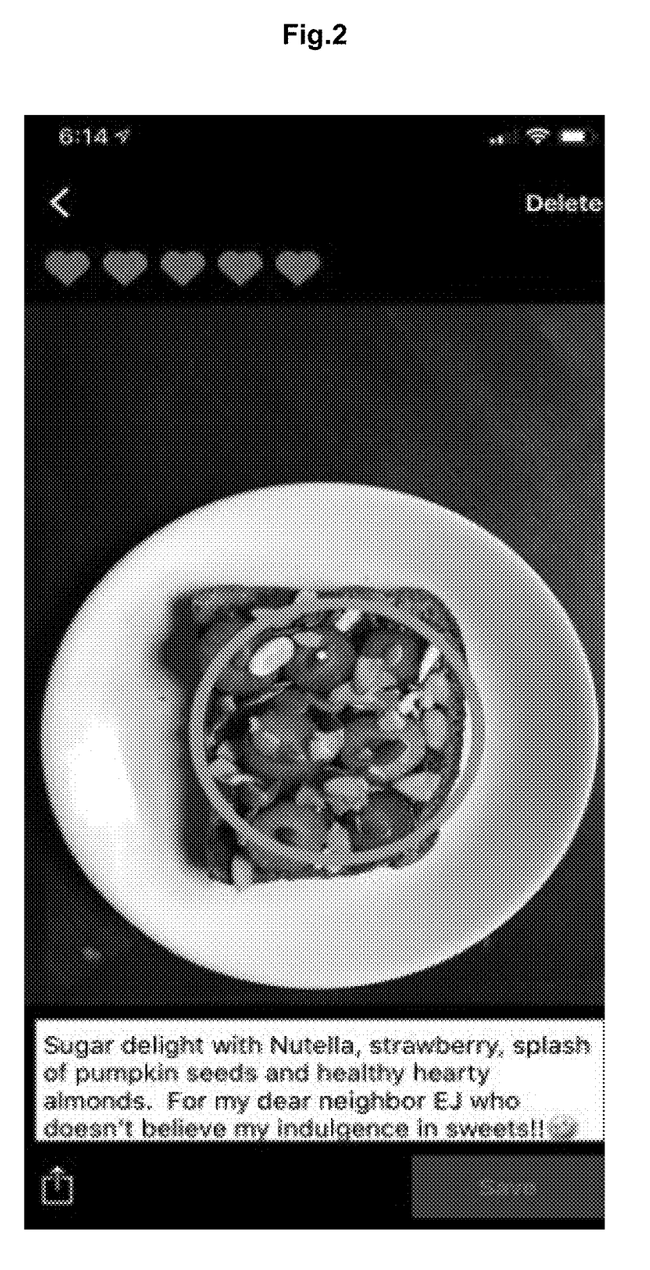
FIG. 2 is a depiction of the graphical user interface (GUI) of one particular embodiment of the tools of the present invention, depicting the visualized selected real-word food quantum overlay on a smart phone digital display as a defined 2-dimensional shape, i.e., a circle. The food is bigger than the circle overlay, which provides guidance to the user to remove certain food amounts outside the circle to eat food volumes that are trackable and consistent.
Figure 3:
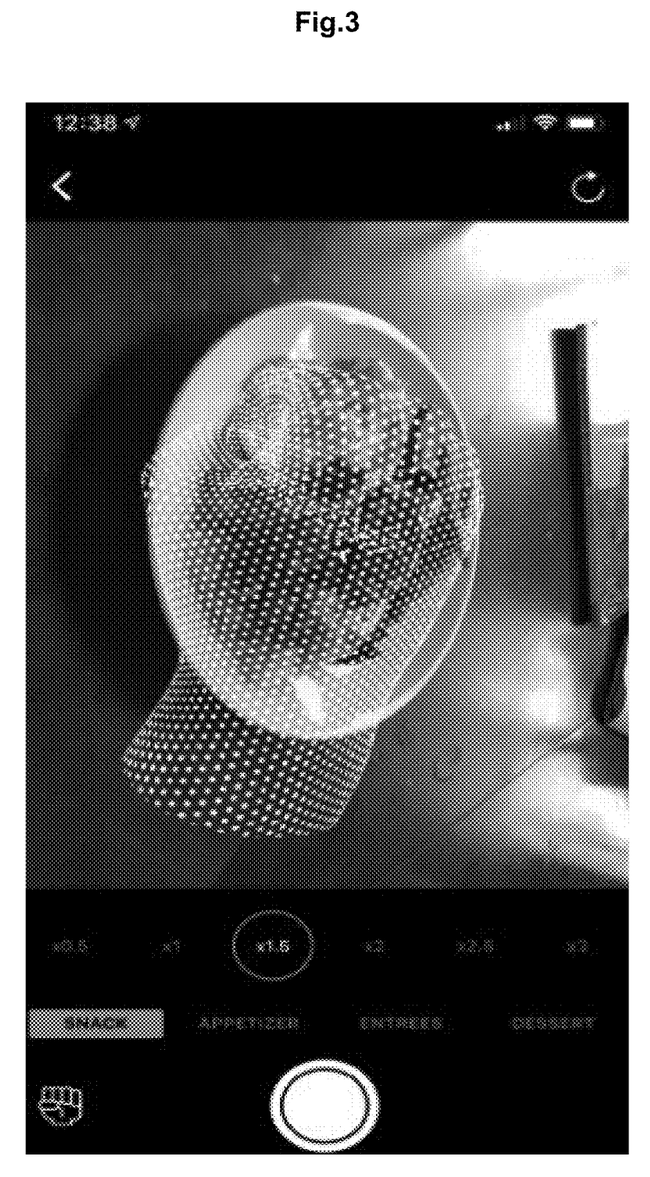
FIG. 3 is a depiction of the graphical user interface (GUI) of one particular embodiment of the tools of the present invention, depicting the visualized selected real-word food quantum overlay on a smart phone digital display as a defined 3-dimensional shape, i.e., a fist. The color of the first corresponds to a specific portion size, or quantum from the quanta series.
Figure 4:
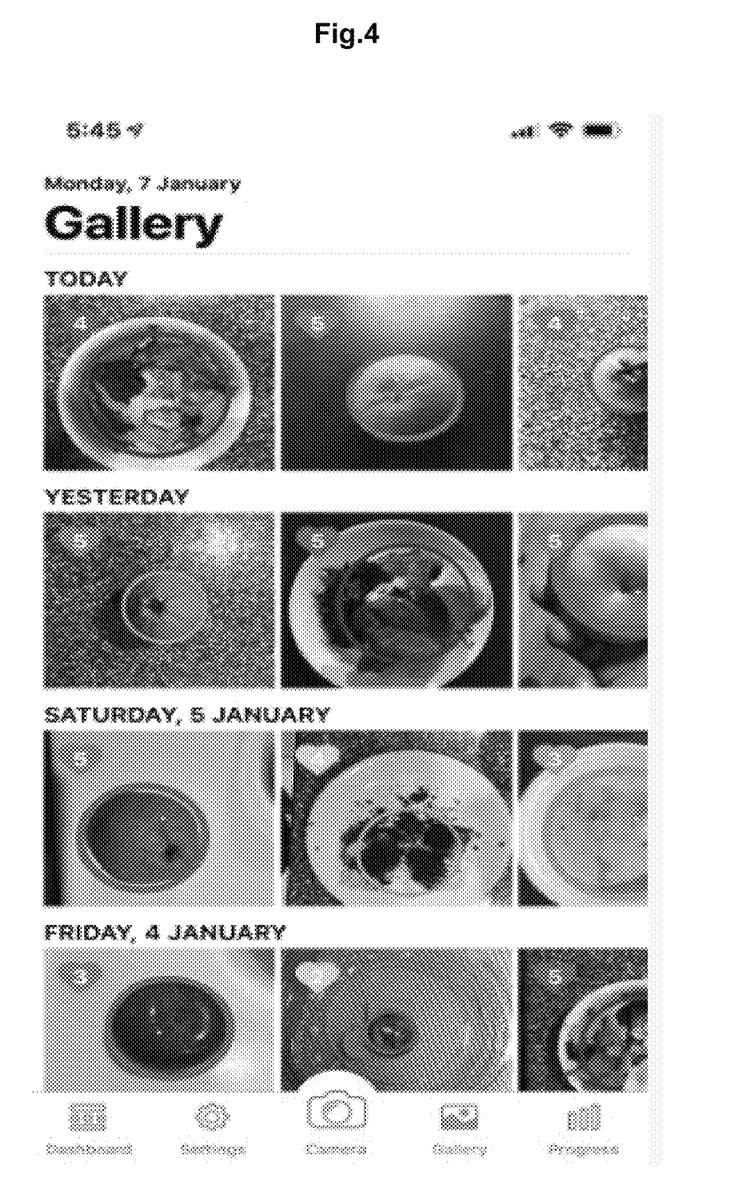
FIG. 4 is a depiction of the graphical user interface (GUI) of one particular embodiment of the tools of the present invention, depicting the gallery of saved visualized selected real-word food quantum overlays for identified times on a smart phone digital display, i.e., creating a journal record.
Figure 5:
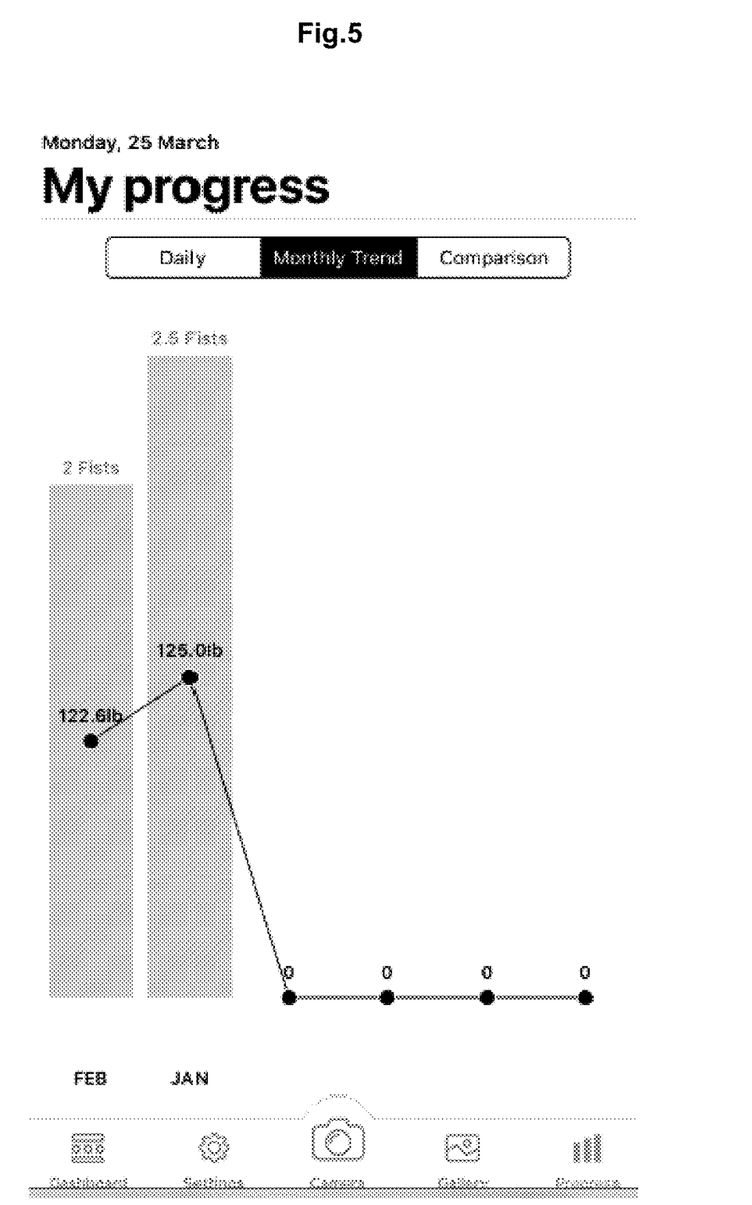
FIG. 5 is a depiction of the graphical user interface (GUI) of one particular embodiment of the tools of the present invention, depicting the progress (as a monthly trend), correlating quantum selection distribution (where the food quantum is based on the user's first) along with weight tracking.

Independent of the utility related to the food quantum tracking tool of the present invention, the ornamental appearance of any novel design provided herein is intended to be part of this invention, for example, each of the views in FIGS. 1 through 5, which may form an independent or combined ornamental appearance of food quantum tracking tool interfaces described herein.

Accordingly, one embodiment of the present invention provide an ornamental design for a food quantum tracking tool interface as shown and described.

EXEMPLIFICATION

Having thus described the invention in general terms, reference will now be made to the accompanying drawings of exemplary embodiments, which are not necessarily drawn to scale, and which are not intended to be limiting in any way.

In this respect, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

EXAMPLE 1

Exemplary/Sample Food Quantum Tracking Tool Within the Scope of the Present Invention The food tracking tools of the present invention may be implemented in a variety of ways. One such implementation provides a mobile application or "app" (i.e., an application software that is executable on a smartphone) that achieves the following steps:

defining a food quanta series for a user;

storing the defined food quanta on a second machine-readable medium;

selecting a single food quantum from the stored food quanta series; and overlaying the selected food quantum on real-world food (RWF) using augmented reality without using a reference marker or reference-based imaging, such that the user is guided to select a definable food quantum, e.g., to achieve a dietary goal.

One particular implementation affords a structured architecture according to the following steps:

Step 1:
User provides personal information such as height, weight, gender, shoe size, birthday.

Step 2:
App calculates user's first circumference based on user's shoe size and defines/creates food quanta series.

Step 3:
App stores personal information and personal first circumference on the server, along with food quanta series.

Step 4:
User opens App Camera function.

Step 5:
User selects 2D or 3D defined shape, e.g., circle or three-dimensionally shaped fist, as informed by step 3, as well as food type (Appetizer, Snack, Dessert, Entrees).

Step 6:
App shows video image (e.g., picture image in active focus and window/frame selection) overlay of food along with a 2D/3D first using augmented reality.

Step 7:
User selects desired quantum (0.5×, 1×, 1.5×, 2.5×, 3× of fist), e.g., according to portion goal.

Step 8
User may adjust food quantum.

Step 9:
User saves overlaid image.

Step 10:
User reviews image. If looks good, proceed to Step 11. If not, go back to Step 6.

Step 11:
User adds description on meal, if desired, and saves image.

Step 12:
App adds saved image into meal gallery.

Step 13:
App processes collected data and updates graphs in Progress function

Step 14:
User may review Progress and adjust their portion goal in Step 7.

As such, the user is guided to select a definable food quantum, e.g., to achieve a dietary goal.

Incorporation By Reference

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A food quantum tracking tool comprising a machine-readable medium having instructions stored thereon for execution by a processor to perform a method comprising the steps of:

defining a food quanta series for a user;

storing the defined food quanta on a second machine-readable medium;

selecting a single food quantum from the stored food quanta series; and overlaying the selected food quantum on real-world food (RWF) using augmented reality without using a reference marker or reference-based imaging, such that the user is guided to select a definable food quantum.

2. The food quantum tracking tool of claim 1, wherein the selected food quantum overlay on the RWF is visualized using a digital display.

3. The food quantum tracking tool of claim 2, wherein the selected food quantum overlay is shown as a defined shape in the visualization.

4. The food quantum tracking tool of claim 1, wherein the method further comprises the step of capturing an image of the overlaid food quantum.

5. The food quantum tracking tool of claim 4, wherein the method further comprises the step of storing said image to create a log.

6. The food quantum tracking tool of claim 1, wherein the step of defining a food quanta series for a user further comprises receiving input directly, providing a personalized defined volume.

7. The food quantum tracking tool of claim 1, wherein the step of defining a food quanta series for a user further comprises receiving input to calculate a personalized defined volume.

8. The food quantum tracking tool of claim 7, wherein the method further comprises the step of collecting shoe size information from the user.

9. The food quantum tracking tool of claim 1, wherein the method further comprises the step of collecting additional information from the user.

10. The food quantum tracking tool of claim 1, wherein the method further comprises the step of selecting a second food quantum for comparison to the single food quantum; and overlaying the selected food quantum on real-world food using augmented reality without using a reference marker or reference-based imaging, to provide additional guidance to the user.

11. The food quantum tracking tool of claim 4, wherein the step of capturing the image utilizes a smart device camera capable of integrating augmented reality.

12. The food quantum tracking tool of claim 11, wherein the defined food quantum is shown on the image as a defined shape.

13. The food quantum tracking tool of claim 1, wherein the machine-readable medium is selected from one or more solid state devices.

14. The food quantum tracking tool of claim 13, wherein the machine-readable medium is one or more network server disks.

15. The food quantum tracking tool of claim 1 comprising a user interface that is a mobile application.

16. A method of food quantum tracking comprising the steps of:
 defining a food quanta series for a user;
 storing the defined food quanta;
 selecting a single food quantum from the stored food quanta series; and
 overlaying the selected food quantum on real-world food (RWF) using augmented reality without using a reference marker or reference-based imaging,
such that the user is guided to select a definable food quantum.

17. The method of claim 16, wherein the selected food quantum overlay on the RWF is visualized using a digital display.

18. The method of claim 17, wherein the selected food quantum overlay is shown as a defined shape in the visualization.

19. The method of claim 16, further comprising the step of capturing an image of the overlaid food quantum.

20. The method of claim 19, wherein the method further comprises the step of storing said image to create a log.

21. The method of claim 16, wherein the step of defining a food quanta series for a user further comprises receiving input directly, providing a personalized defined volume.

22. The method of claim 16, wherein the step of defining a food quanta series for a user further comprises receiving input to calculate a personalized defined volume.

23. The method of claim 22, wherein the method further comprises the step of collecting shoe size information from the user.

24. The method of claim 16, further comprising the step of collecting additional information from the user.

25. The method of claim 16, further comprising the step of selecting a second food quantum for comparison to the single food quantum; and overlaying the selected food quantum on real-world food using augmented reality without using a reference marker or reference-based imaging, to provide additional guidance to the user.

26. The method of claim 19, wherein the step of capturing the image utilizes a smart device camera capable of integrating augmented reality.

27. The method of claim 26, wherein the defined food quantum is shown on the image as a defined shape.

* * * * *